United States Patent
Aono et al.

(10) Patent No.: US 9,945,993 B2
(45) Date of Patent: Apr. 17, 2018

(54) CURVED GRATING, METHOD FOR MANUFACTURING THE SAME, AND OPTICAL DEVICE

(71) Applicant: Hitachi High-Technologies Corporation, Minato-ku, Tokyo (JP)

(72) Inventors: Takanori Aono, Tokyo (JP); Yoshisada Ebata, Tokyo (JP); Shigeru Matsui, Tokyo (JP); Tetsuya Watanabe, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 121 days.

(21) Appl. No.: 14/777,546

(22) PCT Filed: Jan. 30, 2014

(86) PCT No.: PCT/JP2014/052090
§ 371 (c)(1),
(2) Date: Sep. 16, 2015

(87) PCT Pub. No.: WO2014/148118
PCT Pub. Date: Sep. 25, 2014

(65) Prior Publication Data
US 2016/0282526 A1    Sep. 29, 2016

(30) Foreign Application Priority Data
Mar. 19, 2013 (JP) .................................. 2013-057127

(51) Int. Cl.
*G02B 5/18* (2006.01)
*G01N 21/31* (2006.01)
*G02B 1/04* (2006.01)

(52) U.S. Cl.
CPC ........... *G02B 5/1852* (2013.01); *G01N 21/31* (2013.01); *G02B 1/04* (2013.01); *G02B 5/1814* (2013.01);
(Continued)

(58) Field of Classification Search
None
See application file for complete search history.

(56) References Cited

U.S. PATENT DOCUMENTS 3,821,507 A    6/1974    Bratkowski et al.
4,012,843 A *  3/1977    Harada ............... G02B 5/1852
                                              33/19.2

(Continued)

FOREIGN PATENT DOCUMENTS

EP    2 860 557 A1    4/2015
JP    46-375          8/1971
(Continued)

OTHER PUBLICATIONS

European Search Report issued in counterpart European Application No. 14770190.8 dated Sep. 22, 2016 (eight (8) pages).
(Continued)

*Primary Examiner* — Shawn Decenzo
(74) *Attorney, Agent, or Firm* — Crowell & Moring LLP

(57) ABSTRACT

A technique is provided which enables preparation of a curved grating having a desired curvature, by plastically deforming, along a curved substrate, a flat grating prepared by a semiconductor process on a silicon substrate, and which thus prepares a diffraction grating with high accuracy. A silicon flat grating prepared by a semiconductor process is transferred to an amorphous material, and the amorphous material substrate is curved and mounted on a curved fixed
(Continued)

substrate, thus providing a curved grating having a crystalline material in which the generation of a dislocation line is restrained.

7 Claims, 8 Drawing Sheets

(52) U.S. Cl.
CPC ......... *G02B 5/1857* (2013.01); *G02B 5/1861* (2013.01)

(56) References Cited

U.S. PATENT DOCUMENTS

| | | | |
|---|---|---|---|
| 4,330,175 A | 5/1982 | Fujii et al. | |
| 8,390,806 B1* | 3/2013 | Subramanian | G01J 3/0259 |
| | | | 356/301 |
| 9,433,351 B2* | 9/2016 | Yu | A61B 5/0059 |
| 2004/0145820 A1* | 7/2004 | Harwit | G02B 5/09 |
| | | | 359/811 |
| 2005/0073747 A1* | 4/2005 | Suzudo | G02B 5/1833 |
| | | | 359/566 |
| 2009/0194913 A1* | 8/2009 | Chang | B29C 35/0805 |
| | | | 264/447 |
| 2009/0267088 A1* | 10/2009 | Peng | G02B 27/1006 |
| | | | 257/88 |
| 2010/0134889 A1* | 6/2010 | Takayama | G02B 5/1866 |
| | | | 359/576 |
| 2011/0110499 A1 | 5/2011 | Mitsuda et al. | |
| 2012/0085574 A1* | 4/2012 | Park | H05K 3/44 |
| | | | 174/264 |
| 2015/0192713 A1 | 7/2015 | Aono et al. | |

FOREIGN PATENT DOCUMENTS

| | | |
|---|---|---|
| JP | 55-133004 A | 10/1980 |
| JP | 61-72202 A | 4/1986 |
| JP | 8-29610 A | 2/1996 |
| JP | 8-211214 A | 8/1996 |
| JP | 9-5509 A | 1/1997 |
| JP | 2005-283814 A | 10/2005 |
| JP | 2010-25723 A | 2/2010 |
| JP | 2010-261885 A | 11/2010 |
| WO | WO 2008/081555 A1 | 7/2008 |
| WO | WO 2013/183601 A1 | 12/2013 |

OTHER PUBLICATIONS

International Search Report (PCT/ISA/210) dated Mar. 18, 2014, with English translation (four (4) pages).

* cited by examiner

[FIG. 1]
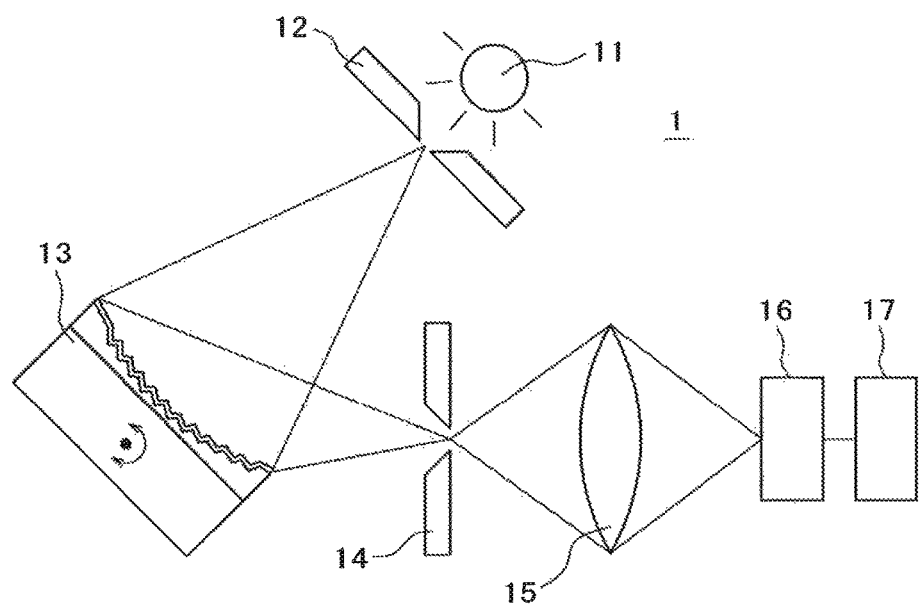
[FIG. 2]
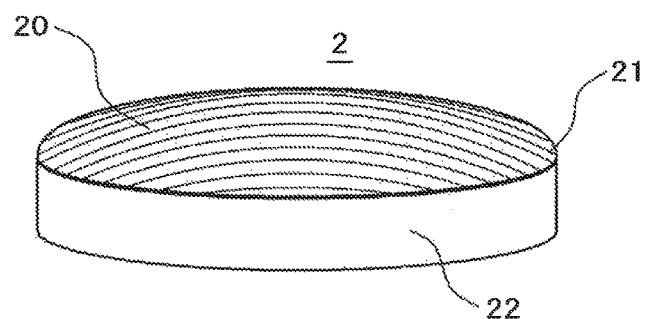

[FIG. 3]
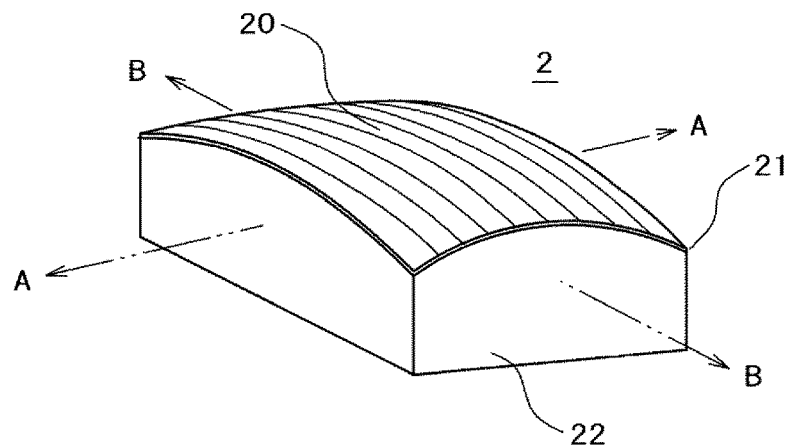
[FIG. 4A]
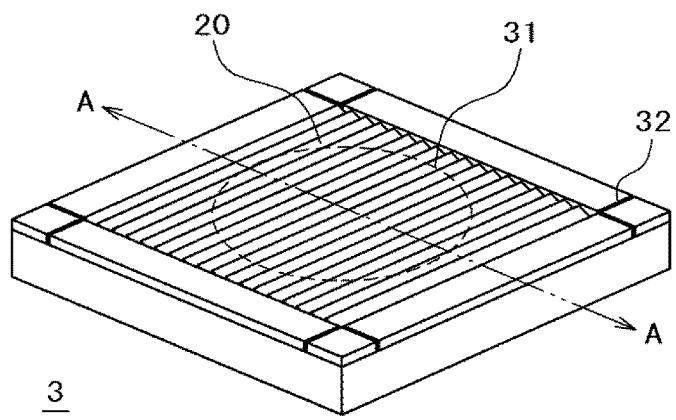
[FIG. 4B]
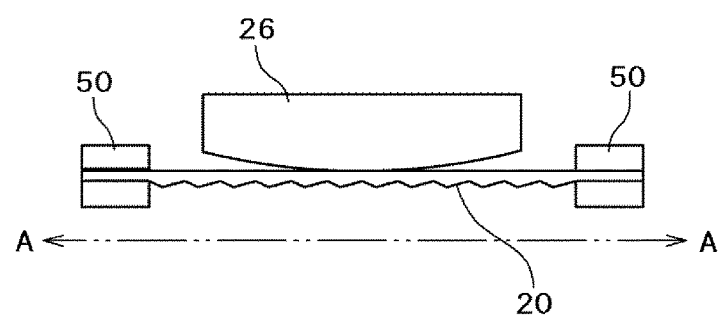

[FIG. 5A]
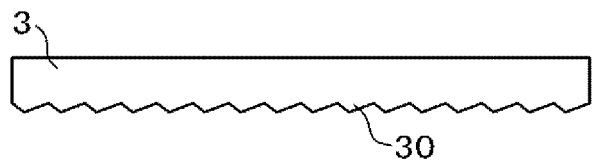
[FIG. 5B]
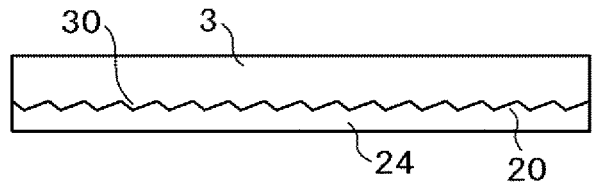
[FIG. 5C]
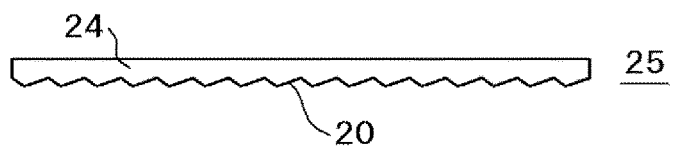
[FIG. 5D]
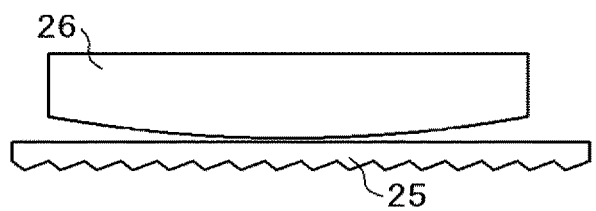
[FIG. 5E]
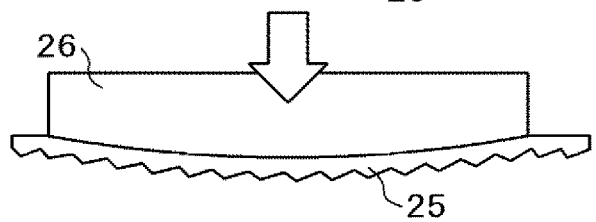
[FIG. 5F]
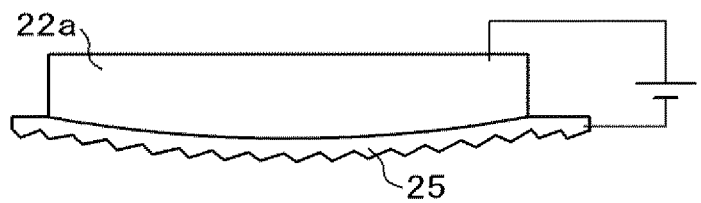
[FIG. 5G]
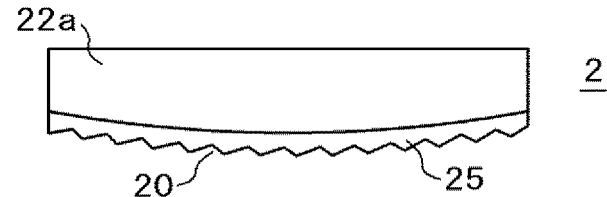

[FIG. 6A]
[FIG. 6B]
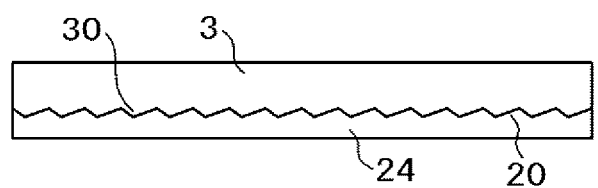
[FIG. 6C]
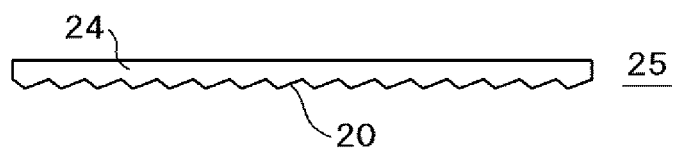
[FIG. 6D]
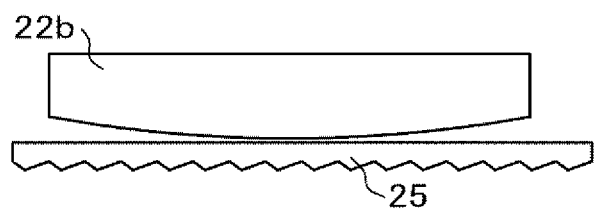
[FIG. 6E]
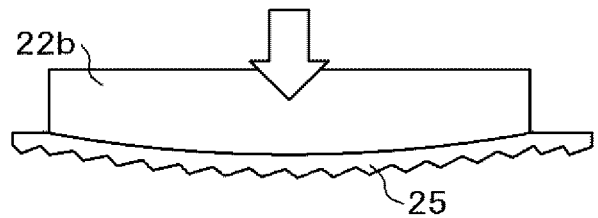
[FIG. 6F]
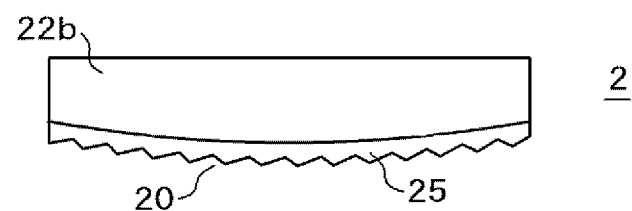

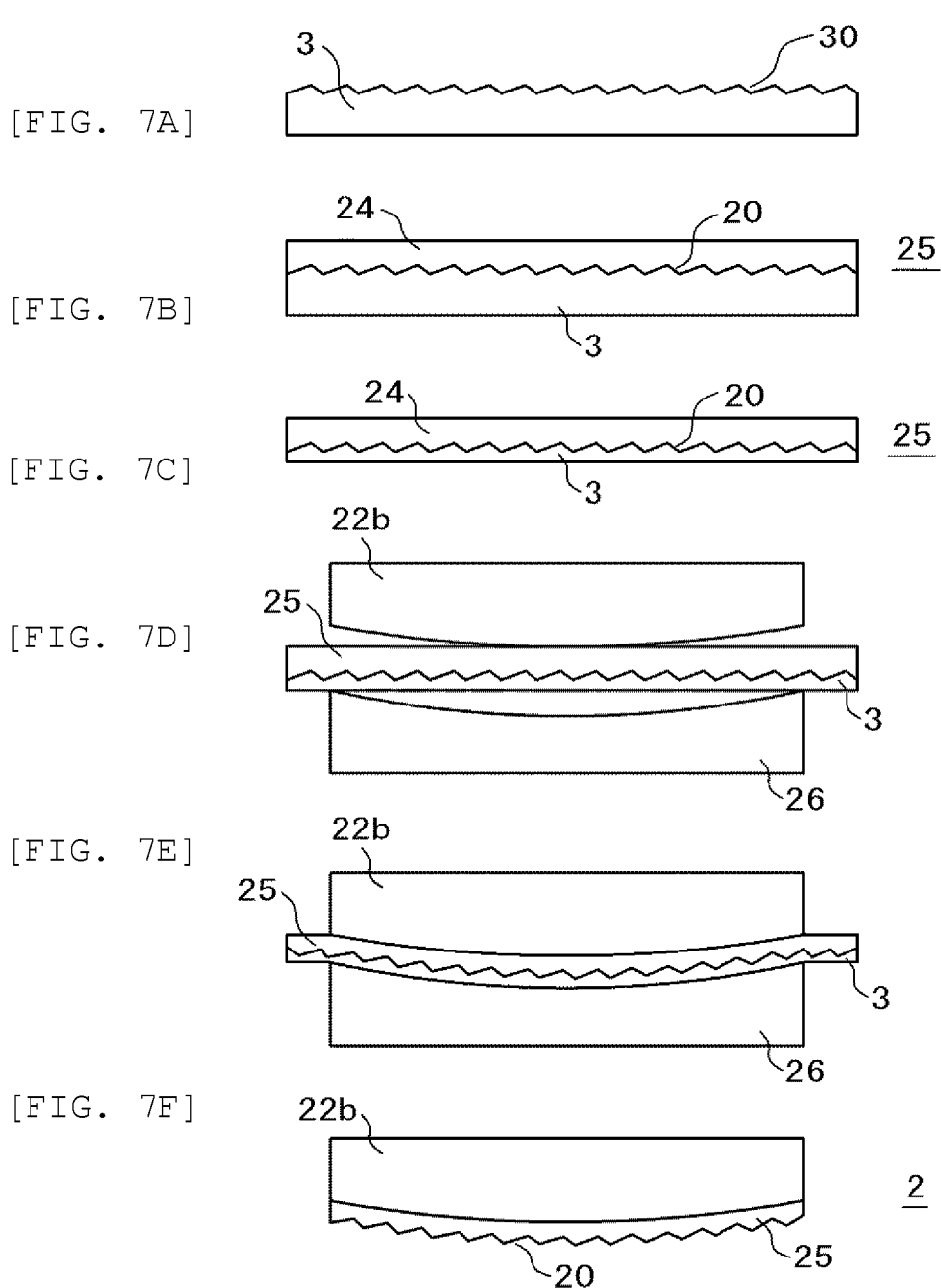

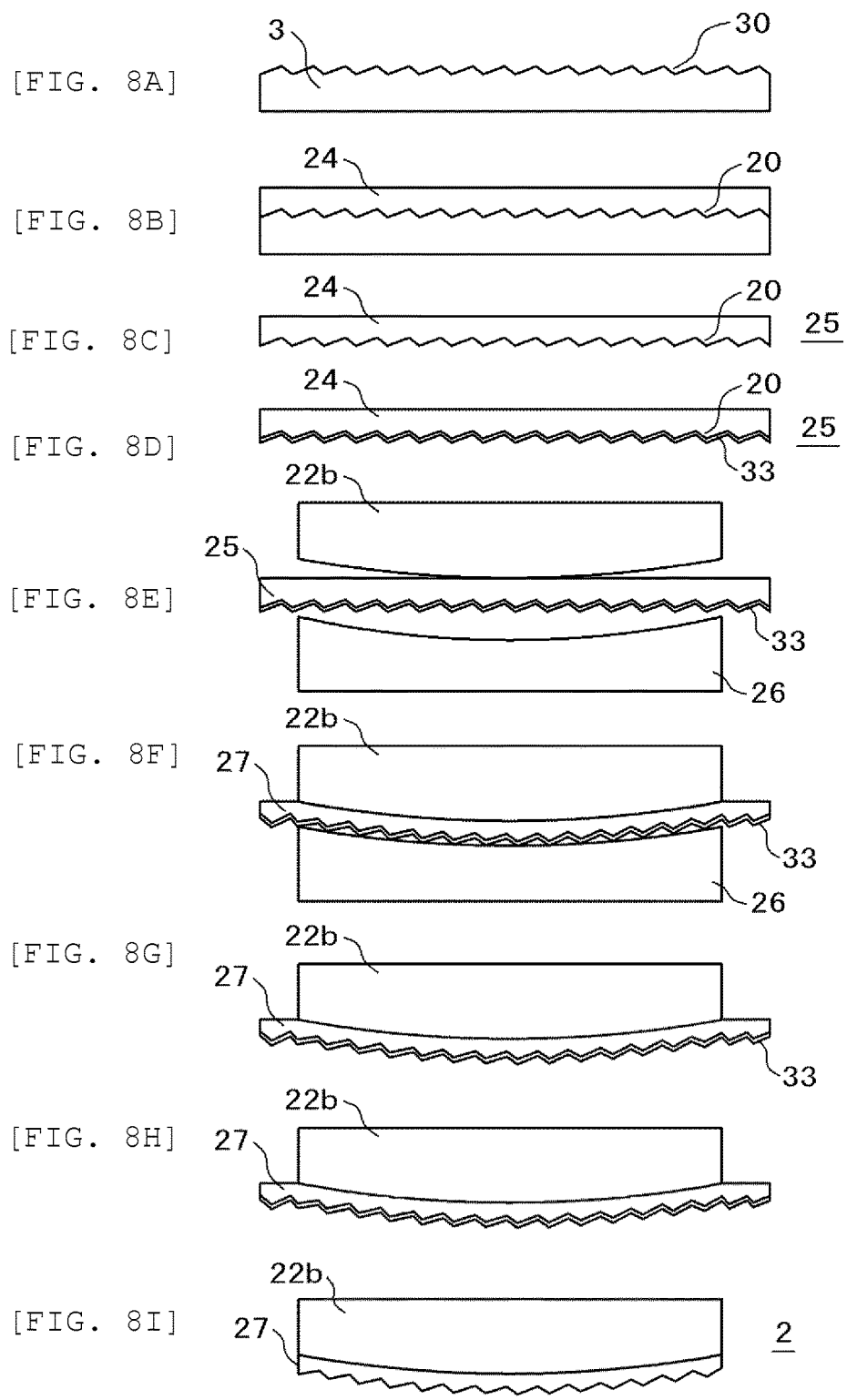

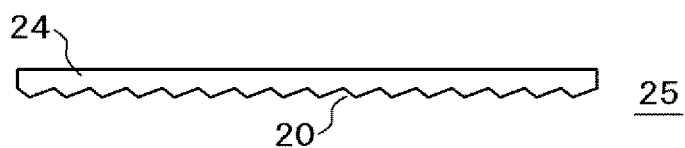
[FIG. 9A]
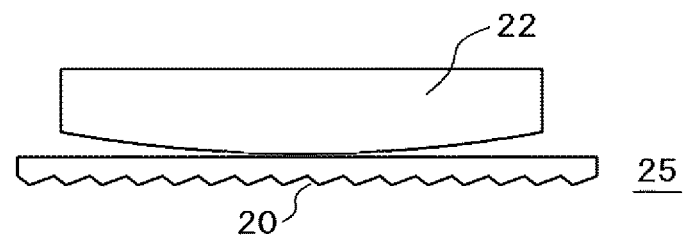
[FIG. 9B]
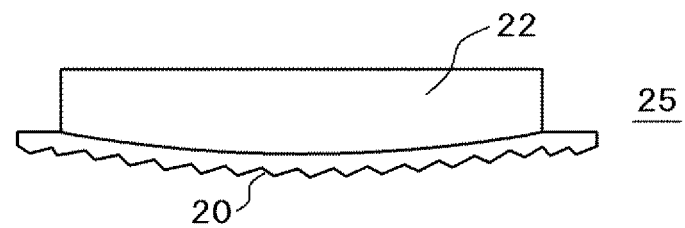
[FIG. 9C]
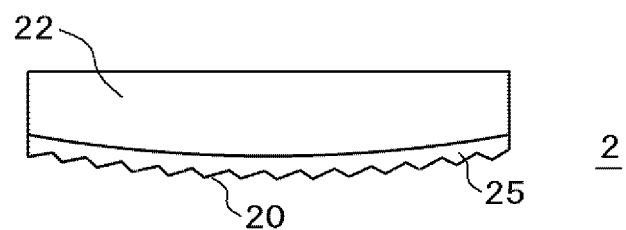
[FIG. 9D]

[FIG. 10A]
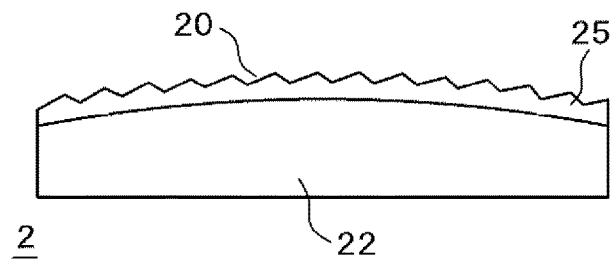
[FIG. 10B]
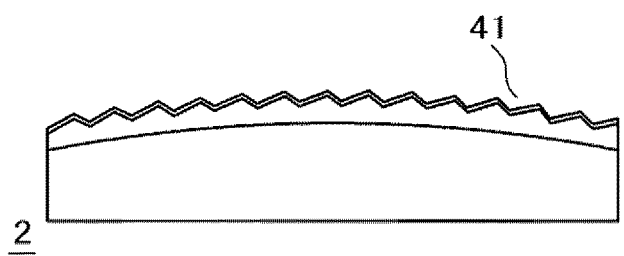
[FIG. 10C]
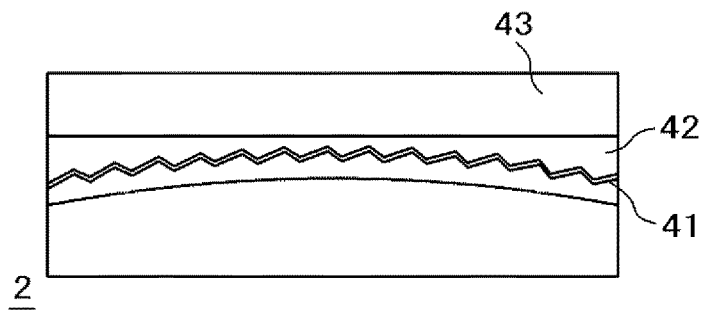
[FIG. 10D]
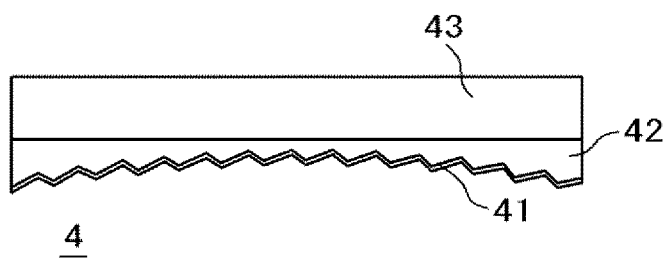

CURVED GRATING, METHOD FOR MANUFACTURING THE SAME, AND OPTICAL DEVICE

TECHNICAL FIELD

The present invention relates to a curved grating, method for manufacturing the same, and an optical device, and particularly to a curved grating which spectrally splits and converges light, and an optical device using the same.

BACKGROUND ART

As the background art in this technical filed, a curved grating, which is an optical element of a spectrophotometer, has both capabilities of spectrally splitting and converging light. Therefore, the number of components can be reduced and the configuration of the device can be simplified.

Conventionally, a curved grating is manufactured by preparing a mold of a diffraction grating by a method in which a curved substrate is carved with a machine such as a ruling engine, and then transferring the carved pattern to a resin, metal or the like.

As a method for preparing a curved grating, WO2008/081555 (PTL 1) discloses a method in which a flat grating and a concave blazed grating are prepared, using semiconductor photolithography and etching processes.

According to JP-A-61-72202 (PTL 2 a diffraction grating pattern is formed on a flexible material such as a resin or thin metal film, which is then attached to a substrate curved to a predetermined curvature, thus forming a mold. This mold is brought in contact with a liquid curved grating material before hardening, and the material is hardened to prepare a curved grating.

According to JP-A-8-29610 (PTL 3), a replica layer (diffraction grating part) using a reactive curing resin is stacked on a flexible substrate, and the flat grating is curved, utilizing the curing contraction of the reactive curing resin.

According to JP-A-9-5509 (PTL 4), a flat grating substrate is transferred to a flexible material such as a silicone resin, which is then fixed to a curved substrate, thus forming a curved grating mold.

JP-A-2010-25723 (PTL 5) discloses an X-ray reflection device having an X-ray reflector which is prepared by heating a silicon substrate to a high temperature in a hydrogen atmosphere so as to plastically deform the silicon substrate into a desired shape, and then stacking a number of the same substrates.

CITATION LIST

Patent Literature

PTL 1: WO2008/081555
PTL 2: JP-A-61-72202
PTL 3: JP-A-8-29610
PTL 4: JP-A-9-5509
PTL 5: JP-A-2010-25723

SUMMARY OF INVENTION

Technical Problem

With the method for manufacturing a curved grating using a semiconductor process disclosed in PTL 1, of the above methods for manufacturing a diffraction grating, it is difficult to accurately prepare a diffraction grating pattern on an arbitrary curved surface. With the techniques described in PTL 2 to PTL 4, pattern accuracy falls at the time of transfer of a curved grating because each of these techniques uses a flexible member in the stage of forming the diffraction grating pattern. Particularly, according to PTL 4, a pattern is transferred onto a flexible material such as a silicone-based resin, which is then fixed to a curved substrate to form a curved grating mold, and the mold is transferred to a curved grating, thus preparing the curved grating. However, the since the flexible material is used, a pattern distortion in the mold occurs due to a fall in pattern accuracy, the transfer of the curved grating, and the pulling of the mold at time of release, and therefore the mold has a short life. Also, according to PTL 5, which describes a method in which a silicon substrate is plastically deformed, a diffraction grating pattern made of silicon is flattened in high-temperature hydrogen atmosphere. Since plastic deformation needs to be used in order to curve a silicon flat grating, a dislocation line is generated and a void or the like is generated in fixing to a curved fixed substrate, thus lowering surface accuracy. In the plastic deformation of the silicon diffraction grating, a dislocation line is generated. Therefore, when pressing and transferring the diffraction grating pattern of the silicon diffraction grating to an amorphous material, a void is generated between the silicon diffraction grating and the amorphous material, obstructing the transfer.

Thus, an object of the invention is to provide a technique which enables preparation of a curved grating having a desired curvature, by plastically deforming, along a curved substrate, a flat grating prepared by a semiconductor process on a silicon substrate, and which thus prepares a diffraction grating with high accuracy.

Solution to Problem

In view of the foregoing problem, the invention has the following characteristics. In a method for manufacturing a diffraction grating pattern, a diffraction grating pattern is formed on a silicon substrate, and the diffraction grating pattern is transferred to an amorphous material, thus preparing a flat grating made of the amorphous material. This flat grating made of the amorphous material is deformed into a curved surface and mounted on a curved fixed substrate, thus preparing a curved grating mold. This curved grating mold is transferred to a metal film or resin, thus preparing a curved grating. As the amorphous material, a glass, metal or the like is used.

In the transfer of the diffraction grating pattern of the silicon flat grating to the amorphous material substrate, thermal deformation of the amorphous material substrate, plastic deformation by application of a load, electroplating with a metal or the like is used. In the case of using thermal deformation or plastic deformation, thermal deformation or plastic deformation is used after the silicon flat grating and the amorphous material substrate are bonded together in order to improve the transfer accuracy of the diffraction grating pattern. By bonding the silicon flat grating and the amorphous material substrate together in advance, lateral shift due to thermal deformation or plastic deformation can be prevented and the transfer accuracy of the diffraction grating pattern can be improved. Also, if the bonding of the silicon flat grating and the amorphous material substrate is carried out in a vacuum atmosphere, the void formed between these can be restrained. The void can also be restrained by forming a vent groove in the silicon diffraction grating to the outside of the substrate corresponding to the diffraction grating pattern. If the vent groove is removed after the diffraction grating pattern is transferred to the amorphous material substrate, diffracted light will not be affected at the time of transfer to the curved grating. Also, the diffraction grating pattern may be used as a vent groove.

In the deformation of the amorphous material, substrate with the diffraction grating pattern transferred thereto, it is possible to restrain the generation of a dislocation line generated by the plastic deformation of the amorphous material such as silicon or quartz into a curved surface. Also, since the amorphous material is used the thermal deformation of the mold is slight, at the time of pattern transfer to the curved grating and therefore accuracy can be improved, and release from the moth can be achieved without raving deformation due to the pulling at the time of release and therefore the life of the mold is improved.

As a method for mounting the amorphous material substrate on the curved fixed substrate after the amorphous material substrate with the diffraction grating pattern transferred thereto is deformed into a curved surface, anodic bonding, direct bonding, or eutectic bonding is used. If a glass is used as the amorphous material, a curved crating mold can be formed by anodic bonding using silicon as the curved fixed substrate. In the case of using direct bonding, the deformation and the bonding with the curved fixed substrate can be prepared in the same process. In direct bonding, if the linear expansion coefficients of the amorphous material substrate and the curved fixed substrate are greatly different in the high-temperature atmosphere, damage occurs due to thermal contraction difference in the cooling process. Therefore, materials having substantially equal linear expansion coefficients are selected for the amorphous material substrate and the curved fixed substrate. Also, if deformation and the direct bonding are carries out simultaneously, the deformation starts from the center of the amorphous material substrate and therefore the bonding area, too, advances from the center toward the outer peripheries. Therefore, since no void is formed between the silicon substrate and the curved fixed substrate, the curved grating mold can be prepared with good surface accuracy.

Although surface accuracy falls compared with direct bonding and anodic bonding, the curved grating mold may be prepared using eutectic bonding, by preparing a solder on the bonding surface between the amorphous material substrate and the curved fixed substrate by sputtering, deposition, electroplating or the like.

The curved grating mold prepared by the above method is transferred to a resin, metal or the like, thus preparing a curved grating.

Advantageous Effect of Invention

According to the invention, a curved grating having a desired curvature can be prepared by plastically deforming, along a curved substrate, a flat grating prepared by a semiconductor process on a silicon substrate. Since the silicon diffraction grating pattern can be used as it is, a highly accurate diffraction grating can be prepared.

BRIEF DESCRIPTION OF DRAWINGS

FIG. 1 is a view showing an outline of a spectrophotometer using a curved grating of the invention.

FIG. 2 is a view showing a mold of the curved grating of the invention.

FIG. 3 is a view showing a mold of a toroidal grating of the invention.

FIG. 4A is a bird's-eye view of a silicon diffraction grating substrate of the invention. FIG. 4B is a side cross-sectional view of the same.

FIGS. 5A-5G are views showing a process of manufacturing a mold of a curved grating according to a first embodiment of the invention.

FIGS. 6A-6F are views showing a process of manufacturing a mold of a curved grating according to a second embodiment of the invention.

FIGS. 7A-7F are views showing a process of manufacturing a mold of a curved grating according to a third embodiment of the invention.

FIGS. 8A-8I are views showing a process of manufacturing a mold of a curved grating according to a fourth embodiment of the invention.

FIGS. 9A-9D are views showing a process of manufacturing a mold of a curved grating according to a fifth embodiment of the invention.

FIGS. 10A-10D are views showing a process of manufacturing a curved grating of the invention.

DESCRIPTION OF EMBODIMENTS

Hereinafter, embodiments according to the invention will be described in detail, using the drawings.

First, the configuration of a spectrophotometer using a diffraction grating will be described.

<<Spectrophotometer>>

FIG. 1 is a schematic view showing an example of spectrophotometer using a curved grating of the invention.

The spectrophotometer is used for measurement of concentration and identification of a substance, by selectively absorbing light with a wavelength unique to a chemical bond of a substance such as a chemical substance or biological substance. As shown in FIG. 1, a spectrophotometer 1 includes a light source 11, slits 12, 14, a diffraction grating 13, a light condensing element 15, a detector 17. The light cast from the light source 11 is cast on the diffraction grating 13 via the slit 12 and spectrally split by the diffraction grating 13. The spectrally split light becomes incident, on a sample 16 via the slit 14 and the light condensing element 15, and the detector 17 measures the absorption (damping) of the wavelength. Here, the diffraction grating 13 is rotated to cast light with a specific wavelength on the sample 16. By curving the diffraction grating 13, the optical elements such as the mirror and light condensing element in the spectrophotometer 1 can be simplified.

<<Curved Grating>>

A curved grating may be a spherical grating or toroidal grating. The specific shape thereof will be described.

[Spherical Grating]

FIG. 2 shows a mold of a spherical grating. Here, a spherical grating is a diffraction grating having a spherical surface with a uniform curvature in any axial direction. As shown in FIG. 2, a curved grating mold 2 is made up of an amorphous material substrate 21 with a diffraction grating pattern 20 formed thereon, and a curved fixed substrate 22. The amorphous material substrate 21 and the curved fixed substrate 22 are fixed together by a connection method chosen from direct bonding, anodic bonding, eutectic bonding, resin bonding or the like. By transferring this curved grating mold 2 to a material which is either a resin or a thin metal film, a concave curved grating is prepared.

[Toroidal Grating]

FIG. 3 shows a mold of a toroidal grating. Here, a toroidal grating is a diffraction grating having a toroidal surface with different curvatures in different axial directions, unlike a spherical grating. The toroidal grating has different, curvatures in direction A-A and direction B-B in the illustration. As shown in FIG. 3, a curved grating mold 2 is made cc of an amorphous material substrate 21 with a diffraction grating pattern 20 formed thereon, and a curved fixed substrate 22. Since the amorphous material substrate 21 is plastically deformed along the curved fixed substrate 22, mounting on a toroidal surface with different curvatures in different axial directions is possible. The amorphous material substrate 21 and the curved fixed substrate 22 are fixed together by a connection method chosen from direct bonding, anodic bonding, eutectic bonding, resin bonding or the like. By transferring this curved grating mold 2 to a material, which is either a resin or a thin metal film, a concave curved grating is prepared.

<<Methods for Manufacturing Curved Grating>>

Next, methods for manufacturing the above curved grating will be described.

The following methods can be used as methods for manufacturing a curved grating represented by the above spherical grating or toroidal grating.

FIG. 4 is a view showing an example of a silicon diffraction grating substrate of the invention. FIG. 4(a) is a bird's-eye view of the silicon diffraction grating substrate. On a silicon flat grating substrate 3, a diffraction grating pattern 20 is formed by a semiconductor process (for example, a process such as photolithography or etching). At this time, a vent groove 32 is formed at a site that does not affect the spectral splitting by the diffraction grating pattern 20. This vent groove 32 is for releasing air bubbles at the time of transfer to an amorphous material substrate 21, and is installed at an outer peripheral part of an area 31 (dashed line) where the amorphous material substrate 21 is deformed into a curved grating. The diffraction grating pattern 20 can be formed to the outer peripheral part of the silicon substrate 3 and used instead of the vent groove 32.

In the examples below, as an amorphous material, metal glass or the like can be used as well as glass.

Also, when a material other than glass is used, a manufacturing method in which a film is formed by deposition, sputtering, electroplating or the like and then the silicon is removed, is employed instead of bonding transfer as in the case of glass. Since metal glass can be formed into a film by deposition, sputtering, electroplating or the like, a diffraction grating pattern can be formed. The metal glass may include Zr—Cu—Al—Ni, Pd—Ni—P and the like.

FIG. 4 (b) is a view showing a cross-sectional view taken along direction A-A when the silicon flat grating 3 is rotated 180 degrees and turned upside down.

The diffraction grating pattern 20 has the peripheral parts thereof supported by a support plate 50. A convex part of a curved substrate 26 made up of the amorphous material substrate 21, described below, is abutted and pressed against the surface where the diffraction grating pattern 20 is not formed (area indicated by the circular dashed line 31 in FIG. 4 (a)) thus curving the diffraction grating pattern 20. Details thereof will be described below.

Examples 1 to 3 described below are examples in which a curved grating mold 2 is prepared by forming a diffraction grating pattern by transfer using a silicon substrate. Example 4 is an example in which a curved grating mold 2 is prepared by forming a diffraction grating pattern without using a silicon substrate.

Example 1

The method for manufacturing a curved grating mold 2 in Example 1 will be described using FIG. 5.

First, a diffraction grating pattern 30 having a waved shape is formed on a bulk silicon substrate 3 by a semiconductor process (for example, photolithography or etching) (FIG. 5(a)).

After the diffraction grating pattern is prepared, the silicon substrate is bonded to a glass substrate 24 and heated to around the softening point. Thus, the shape similar to the diffraction grating pattern 30 formed on the silicon substrate is transferred to the glass substrate 24, forming a diffraction grating pattern 20 (FIG. 5(b)).

After the transfer, the silicon substrate 3 is removed by etching, thus preparing a glass diffraction grating 25 (FIG. 5(c)).

A desired curved substrate 26 is installed on the back side of the surface where the diffraction grating pattern 20 is formed, of the glass diffraction grating 25 (FIG. 5(d)). At this point, though not shown in this illustration, the support plate 50 of the diffraction grating pattern. 20 is prepared in the state of FIG. 4(b).

By applying a high temperature at which the glass is in a viscoelastic range in this state, the glass diffraction grating 25 is deformed (FIG. 5(e)).

Next, the curved substrate 26 is detached and a silicon curved fixed substrate 22a installed. The glass diffraction grating 25 and the silicon curved fixed substrate 22a are anodic-bonded (FIG. 5(f)). In anodic bonding, as illustrated, the curved fixed substrate 22a and the glass diffraction grating 25 are both used as electrodes and a current is applied between the two electrodes, thus bonding the two together.

Finally, an unnecessary part of the glass diffraction grating 25 is removed, forming a curved grating mold 2 (FIG. 5(g)).

As the silicon substrate 3 and the class substrate 24 are bonded together to transfer the diffraction grating pattern 30, there is no misalignment between the substrates and the diffraction grating pattern 30 can be transferred with high accuracy.

Example 2

Next, the method for manufacturing a curved grating mold 2 in Example 2 will be described using FIG. 6. A diffraction grating pattern 30 having a waved shape is formed on a bulk silicon substrate 3 by a semiconductor process (for example, photolithography or etching) (FIG. 6(a)).

After the diffraction grating pattern is prepared, the silicon substrate is bonded to a glass substrate 24 and heated to around the sot softening point. Thus, the shape similar to the diffraction grating pattern 30 formed on the silicon substrate is transferred to the glass substrate 24, forming a diffraction grating pattern 20 (FIG. 6(b)).

After the transfer, the silicon substrate 3 is removed by etching, thus preparing a glass flat grating 25 (FIG. 6 (c)).

A desired glass curved, fixed substrate 22b is installed on the back side of the surface where the diffraction grating pattern 20 is formed, of the glass diffraction grating 25 (FIG. 6(d)). At this point, though not shown in this illustration, the support plate 50 of the diffraction grating pattern 20 is prepared in the state of FIG. 4(b).

By applying a high temperature at which the glass is in a viscoelastic range in this state, the glass diffraction grating 25 is deformed (FIG. 6(e)).

At this point, the glass diffraction grating 25 and the glass curved, fixed substrate 22b can be fixed together by heat. The glass diffraction grating 25 is deformed and fixed to the curved fixed substrate 22b from a center part and therefore can be fixed without a void. Finally, an unnecessary part of the glass diffraction grating 25 is removed, forming a curved grating mold 2 (FIG. 6(f)).

Here, a characteristic of this example is that, since the glass curved fixed substrate 22b is used, which has the same linear expansion coefficient as the glass flat grating 25, damage at the time of cooling from the high temperature can be prevented.

Example 3

Next, the method for manufacturing a curved grating mold 2 in Example 3 will be described using FIG. 7. A diffraction grating pattern 30 having a waved shape is formed on a bulk silicon substrate 3 by a semiconductor process (for example, photolithography or etching) (FIG. 7(a)).

After the diffraction grating pattern is prepared, the silicon substrate is bonded to a glass substrate 24 and heated to around the softening point. Thus, the shape similar to the diffraction grating pattern 30 formed on the silicon substrate is transferred to the glass substrate 24, forming a diffraction grating pattern 20 on the glass substrate 24 (FIG. 7(b)).

After the transfer, the silicon substrate 3 is formed into a thin film by grinding or etching (FIG. 7(c)).

A desired glass curved fixed substrate 22h is installed on the back side of the surface where the diffraction grating pattern 20 is formed, of the glass diffraction grating 25, and a concave curved substrate 26 having a symmetrical shape to the curved fixed substrate 22b is installed on the silicon substrate 3 side (FIG. 7(d)).

By applying a high temperature at which the glass is in a viscoelastic range in this state, the glass diffraction grating 25 is deformed (FIG. 7(e)).

At this point, the glass diffraction grating 25 and the glass curved fixed substrate 22b can be fixed together by heat. The glass diffraction grating 25 is deformed and fixed to the curved fixed substrate 22b from a center part and therefore can be fixed without a void. Finally, an unnecessary part of the glass diffraction grating 25 is removed by etching the silicon substrate 3, forming a curved grating mold. 2 (FIG. 7(f)).

Here, a characteristic of this example is that, since the diffraction grating patterns 20, 30 do not contact the curved fixed substrate 22b and the concave curved substrate 26, the glass diffraction grating 25 can be formed into a desired curved, shape with high accuracy.

Also, after the silicon substrate 3 and the glass substrate 24 are bonded together and the silicon substrate 3 is formed into a thin film, the curved fixed substrate 22b and the concave curved substrate 26 are installed and a high temperature at which the glass shows viscoelasticity is applied. Thus, it is possible to form a curved grating mold 2 by simultaneously carrying out the transfer of the diffraction grating pattern 30 to the glass substrate 24, the deformation of the glass substrate 24, and the fixing of the glass substrate 24 and the curved fixed substrate 22b.

Example 4

Next, the method for manufacturing a curved, grating mold 2 in Example 4 will be described using FIG. 8. A diffraction grating pattern. 30 is formed on a bulk silicon substrate 3 by a semiconductor process (for example, photolithography or etching) (FIG. 8(a)).

After the diffraction grating pattern is prepared, the silicon substrate is bonded to a glass substrate 24 and heated to around the softening point, thus forming a diffraction grating pattern 20 on the glass substrate 24 (FIG. 8 (b)).

After the transfer, the silicon substrate 3 is removed by grinding or etching (FIG. 8 (c)).

On a surface where the diffraction grating pattern 20 is formed, of a glass diffraction grating 25, a material which is highly temperature-resistant and hard to deform, such as silicon or tungsten, is formed into a film as a protection film 33 by sputtering (FIG. 8 (d)).

A desired glass curved fixed substrate 22h is installed on the back of the surface were the diffraction grating pattern 20 is formed, of the glass diffraction grating 25, and a concave curved substrate 26 having a symmetrical shape to the curved fixed substrate 22b is installed on the protection film 33 side (FIG. 8(e)).

By applying a high temperature at which the glass is in a viscoelastic range in this state, the glass diffraction grating 25 is deformed (FIG. 8(f)). At this point, the glass flat grating 25 and the glass curved fixed substrate 22b can be fixed together by heat. Also, the diffraction grating pattern 20 is protected by the projection film 33 and therefore is relatively less subject to damage from the concave curved substrate 26. The glass diffraction grating 25 is deformed and fixed to the curved fixed substrate 22b from a center part and therefore can be fixed without a void.

Next, the concave curved substrate 26 is removed (FIG. 8(g)) and the protection film. 33 is removed by etching (FIG. 8(h)).

Finally, an unnecessary part of a glass curved grating 27 is removed, forming a curved grating mold 2 (FIG. 8(i)).

Here, a characteristic of this example is that the projection film 33 is a thin film and that the glass diffraction grating 25 can be formed into a desired curved shape with high accuracy.

Example 5

Next, the method for manufacturing a curved grating mold in Example 5 will be described using FIG. 9. This example is different from the above Examples 1 to 3 in that the processes such as the formation of a diffraction grating pattern on a silicon substrate and the transfer of the diffraction grating pattern to a glass substrate are not used.

First, a diffraction grating pattern 20 is formed on a bulk glass substrate 24 by a semiconductor process (for example, photolithography or etching), thus forming a glass diffraction grating 25 (FIG. 9 (a)).

A desired glass curved fixed substrate 22 is installed on the back side of the surface where the diffraction grating pattern 20 is formed, of the glass diffraction grating 25 (FIG. 9(b)). At this point, though not shown in this illustration, the support plate 50 of the diffraction grating pattern 20 is prepared in the state of FIG. 4 (b).

By applying a high temperature at which the glass is in a viscoelastic range in this state, the glass diffraction grating 25 is deformed (FIG. 9(c)). At this point, the glass diffraction grating 25 and the glass curved fixed substrate 22 can be fixed together by heat. The glass diffraction grating 25 is deformed and fixed to the curved fixed substrate 22 from a center part and therefore can be fixed without a void.

Finally, an unnecessary part of the class diffraction grating 25 is removed, forming a curved grating mold 2 (FIG. 9(d)).

Here, a characteristic of this example is that, since the glass diffraction grating 25 is worked by a semiconductor process (for example, photolithography or etching), the processes of forming a diffraction grating pattern on a silicon substrate, bonding to a glass substrate, and transfer, described in Examples 1 to 3, can be omitted.

Hereinafter, an example in which a curved grating is prepared, using the curved grating mold 2 prepared in the above Examples 1 to 5, will be described.

Example 6

The method for manufacturing a curved grating 4 using the curved grating mold 2 described in Examples 1 to 5 will be described, using FIG. 10.

The curved grating mold 2 formed by one of the methods described in Example 1 to 5 is prepared (FIG. 10(a)).

A release layer is formed on the surface of the curved grating mold 2 and a reflection film 41 is formed on the release layer (FIG. 10 (b)). The release laser is provided to facilitate release when detaching a resin 42 and a fixed substrate 43 from the curved grating mold 2, described below using FIG. 10 (d).

A liquid curing resin 42 and a fixed substrate 43 are installed on the reflection film 41 (FIG. 10(c)).

After the resin is cured, the resin 42 and the fixed substrate 43 are detached from the curved grating mold 2, thus manufacturing a curved grating 4 (FIG. 10(d)). A flexible metal film may be used instead of the resin. Also, after the diffraction grating pattern 20 is transferred to the resin 42 using the curved grating mold 2 and by a technique such as nano-imprinting, the reflection film 41 may be formed on the surface thereof.

REFERENCE SIGNS LIST

1 . . . spectrophotometer
2 . . . curved grating mold
3 . . . silicon flat grating substrate
4 . . . curved grating
11 . . . light source
12, 14 . . . slit
13 . . . curved grating
15 . . . condensing lens
16 . . . sample
17 . . . detector
20 . . . diffraction grating pattern
21 . . . amorphous material substrate
22 . . . curved fixed substrate
24 . . . amorphous material substrate
25 . . . amorphous material diffraction grating substrate
26 . . . curved substrate
30 . . . diffraction grating pattern
31 . . . curved grating area
32 . . . vent groove
41 . . . reflection film
42 . . . resin
43 . . . fixed substrate
50 . . . support plate

The invention claimed is:

1. A method for manufacturing a curved grating, the method comprising:
forming a diffraction pattern on a silicon substrate;
superimposing the silicon substrate with the diffraction pattern formed thereon and an amorphous material substrate on each other in such a way that the diffraction pattern faces a face side of the amorphous material substrate, and transferring the diffraction pattern to a main surface of the amorphous material substrate;
pressing a curved substrate having a convex curved surface on one main surface against a surface facing the surface of the amorphous material substrate without the diffraction pattern transferred thereto while abutting the one main surface side, and thereby curving the amorphous material substrate;
fixing a convex curved surface facing the one main surface of the curved amorphous material substrate, using a convex curved surface of a fixed substrate having the convex curved surface, and thereby forming a curved grating mold; and
forming longitudinal vent grooves on the silicon substrate in an area that is immediately adjacent to but outside of the diffraction grating pattern, the longitudinal vent grooves being
configured to release gas bubbles that are generated at the time of the transferring of the diffraction grating pattern, and
perpendicular to one another.

2. The method for manufacturing the curved grating according to claim 1, wherein in the superimposing step, the diffraction pattern is transferred to the main surface of the amorphous material substrate while applying heat.

3. The method for manufacturing the curved grating according to claim 1, wherein the fixed substrate is made of a silicon material.

4. The method for manufacturing the curved grating according to claim 1, wherein the fixed substrate is made of the amorphous material.

5. The method for manufacturing the curved grating according to claim 1, wherein in the pressing step,
a combined substrate in which the silicon substrate having the diffraction pattern formed thereon and being formed into a thin film and the amorphous material substrate are superimposed on each other in such a way that the diffraction pattern faces the face side of the amorphous material substrate, is held and pressed between a convex curved substrate having a convex curved surface on one main surface, and a concave curved substrate having a curvature of the convex surface.

6. The method for manufacturing the curved grating according to claim 5, wherein the superimposing step further comprises forming a protection film on the main surface of the amorphous material substrate having the diffraction pattern transferred thereto, after the diffraction pattern is transferred to the main surface of the amorphous material substrate.

7. A curved grating comprising:
a substrate having a diffraction pattern provided on a concave surface;
a reflection film provided to cover the concave surface; and
a fixed substrate to which the substrate is fixed, wherein
the diffraction pattern is formed on a silicon substrate;
the silicon substrate is superimposed with the diffraction pattern formed thereon and an amorphous material substrate on each other in such a way that the diffraction pattern faces a face side of the amorphous material substrate,
the diffraction pattern is transferred to a main surface of the amorphous material substrate,
a curved substrate having a convex curved surface on one main surface is pressed against a surface facing the surface of the amorphous material substrate without the diffraction pattern transferred thereto while abutting the one main surface side, and thereby curving the amorphous material substrate, a convex curved surface facing the one main surface of the curved amorphous material substrate is fixed, a convex curved surface of a fixed substrate having the convex curved surface forms a curved grating mold, a solder layer is disposed on a bonding surface that is located directly between the amorphous material substrate and the convex curved surface of the fixed substrate, and longitudinal vent grooves are formed on the silicon substrate in an area that is immediately adjacent to but outside of the diffraction grating pattern, the longitudinal vent grooves being
- configured to release gas bubbles that are generated at the time of the transferring of the diffraction grating pattern, and
- perpendicular to one another.

\* \* \* \* \*